(12) United States Patent
Tontarra

(10) Patent No.: US 6,699,254 B1
(45) Date of Patent: Mar. 2, 2004

(54) SURGICAL INSTRUMENT

(75) Inventor: Thomas Tontarra, Wurmlingen (DE)

(73) Assignee: Tontarra Medizintechnik GmbH, Wurmlingen (DE)

( * ) Notice: Subject to any disclaimer, the term of this patent is extended or adjusted under 35 U.S.C. 154(b) by 137 days.

(21) Appl. No.: 09/675,361

(22) Filed: Sep. 29, 2000

(30) Foreign Application Priority Data

Oct. 13, 1999 (DE) .......................... 199 49 422

(51) Int. Cl.[7] ............................................... A61B 17/00
(52) U.S. Cl. .......................................................... 606/83
(58) Field of Search ........................... 606/83, 170, 171, 606/184, 208

(56) References Cited

U.S. PATENT DOCUMENTS

| | | | | |
|---|---|---|---|---|
| 5,584,844 A | * | 12/1996 | Weisshaupt | 606/170 |
| 5,961,531 A | * | 10/1999 | Weber et al. | 604/22 |
| 6,102,925 A | * | 8/2000 | Oren et al. | 606/170 |
| 6,126,674 A | * | 10/2000 | Janzen | 606/1 |

* cited by examiner

Primary Examiner—Kevin Shaver
Assistant Examiner—Melba Bumgarner

(57) ABSTRACT

The invention relates to a surgical instrument with a main part and at least one movable part movable relative thereto, with a handle arranged on the main part and having a stationary handle portion and a handle portion an actuatable handle portion which actuates the movable part, and a locking device in which, in a first position, the movable part is arranged in an initial position, and in a second position, the movable part is changed over into a cleaning position and the movable part in this position is arranged captive with respect to the main part.

25 Claims, 8 Drawing Sheets

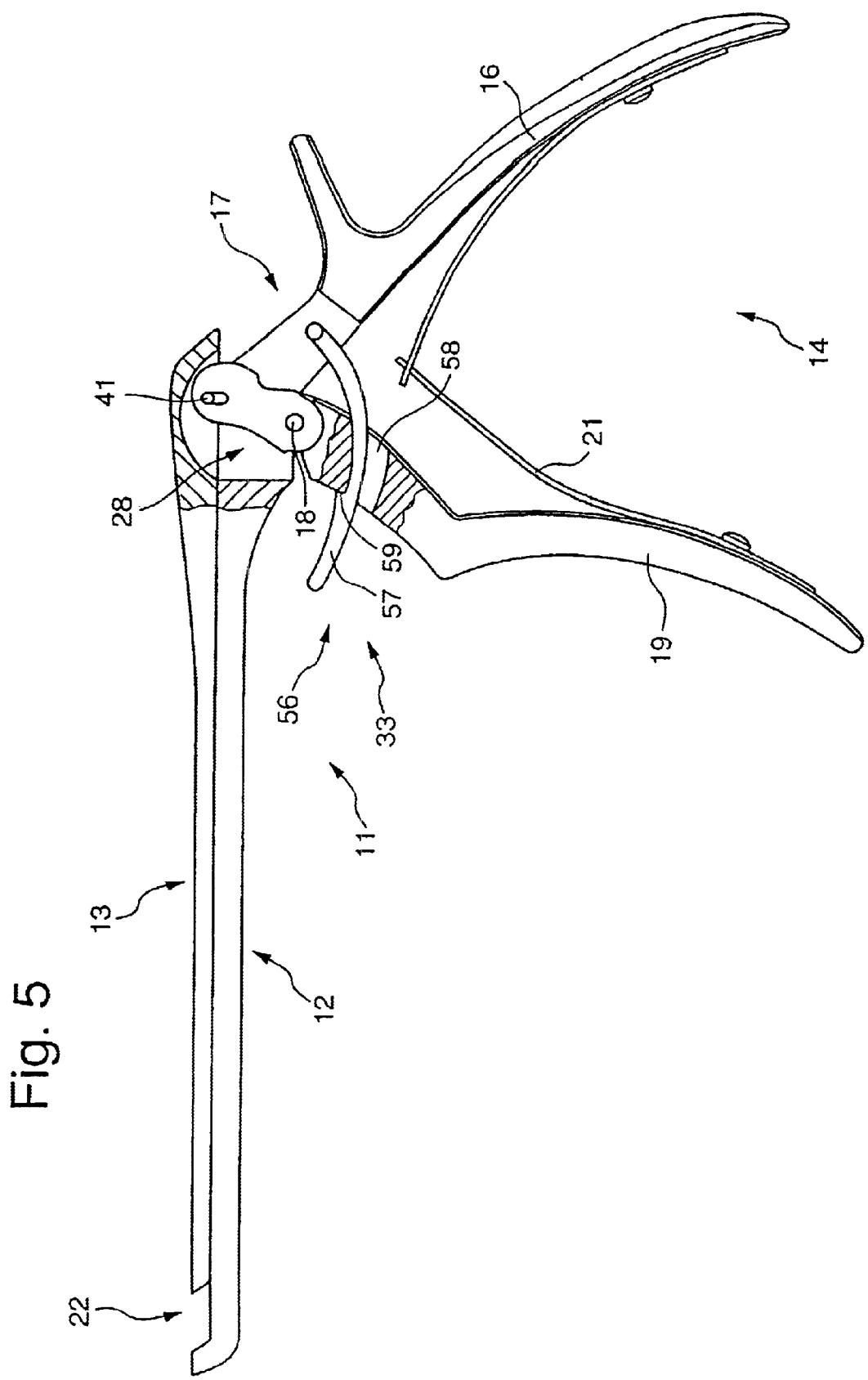

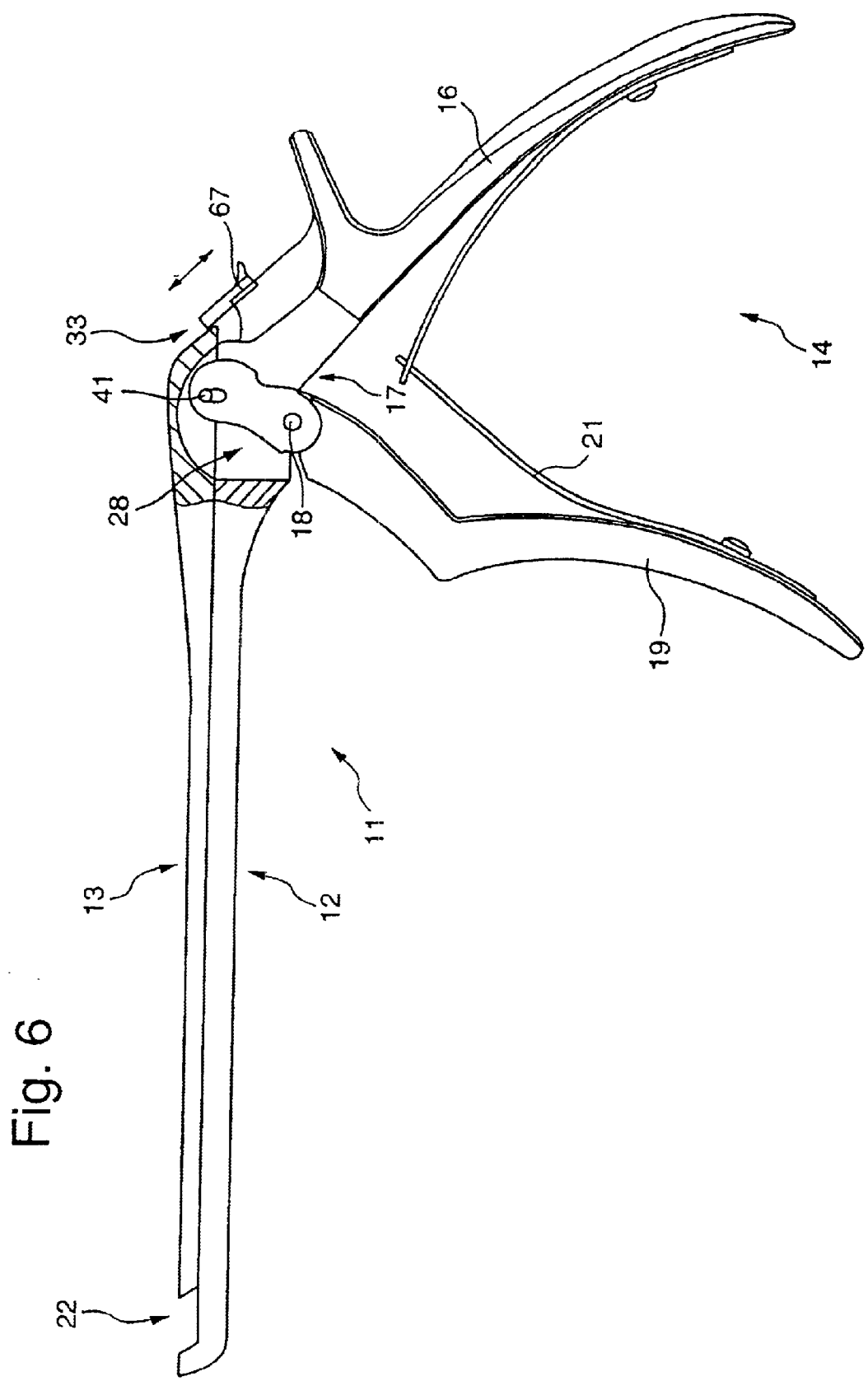

SURGICAL INSTRUMENT

CROSS-REFERENCES TO RELATED APPLICATIONS

Not applicable.

STATEMENT REGARDING FEDERALLY SPONSORED RESEARCH OR DEVELOPMENT

Not applicable.

BACKGROUND OF THE INVENTION

The invention relates to a surgical instrument the fields of surgical instruments, and more particularly, to surgical instruments for cutting and removing tissue, bone and the like during surgery.

Technical Field

Such surgical instruments are known, for example, through the Janit company. With these surgical instruments, punches are concerned which are used to remove tissue, bone or the like in surgical operations. These devices have a main part and at least one part movable relative thereto, a so-called slider, and also a handle which has a stationary handle portion connected to the main part and an actuatable handle portion connected to the movable part. The movable part is closed and opened relative to the main part by opening and closing the handle portion, and the removal of tissue, bone or the like, for example, is made possible during the closing movement.

Such surgical instruments have to be cleaned and sterilized after each surgical operation, in order to prevent the transmission of infections or the like in further operations. However, these instruments have the disadvantage that the movable part is not releasable from the main part, so that bacteria can collect in the region of guides between the movable part and the main part.

Surgical instruments are also known in which the movable part can be completely released and removed from the main part for cleaning and sterilization. The main part and the movable part are then respectively provided with identification marks, so that an allocation of the movable part to the main part is possible after cleaning and sterilizing. This is required because the surgical instruments are finish ground in the assembled state in order to make possible a smooth transition between the main part and the moving part. This has the consequence that a time-consuming allocation of the moving parts to the main parts is required when many instruments are to be cleaned.

BRIEF SUMMARY OF THE INVENTION

The invention therefore has as its object to provide a surgical instrument which can be dismantled for cleaning and sterilization, which does not require an allocation of the parts, and which is simple to manipulate.

This object is attained according to the invention by a surgical instrument comprising a main part, at least one part movable relative thereto, a handle arranged on the main part and having a stationary handle portion, an actuatable handle portion which actuates the movable part, and a locking device in which in a first position the movable part is arranged in an initial position and in a second position the movable part is changed over into a cleaning position and the movable part is in this position arranged captive with respect to the main part.

By the arrangement according to the invention of a locking device, and of the captive configuration of the movable part with respect to the main part, it can be made possible that the surgical instrument can be arranged mutually separated in a simple manner, at least as regards the main part and movable part, for cleaning and sterilization, the surgical instrument meanwhile remaining as a unit. An expensive allocation process after the cleaning and sterilization can thereby be avoided. Furthermore, a surgical instrument can be provided which fulfills hygienic requirements. Moreover, by the configuration of the locking device, a surgical instrument can be provided which corresponds in handling to the prior art instruments, so that no adaptation by the operator is required. Furthermore, a simple manipulation is made possible for the changing over of the movable part with respect to the main part in a cleaning position. Such surgical instruments can be usable for all fields of medicine. The constitution according to the invention can be provided for all surgical instruments in which a main part and a movable part are provided and which can be at least partially disassembled for cleaning.

According to an advantageous development of the invention, it is provided that the movable part and the actuatable handle portion are arranged pivotable to each other by means of an articulated connection. Thereby, the articulated connection already present for the actuation of the movable part can advantageously be used at the same time for the arrangement of the movable part in a cleaning position with respect to the main part. Alternatively, it can be provided that instead of the jointed, slide, or hinge type of articulated connection, further connecting mechanisms can be provided which arrange the movable part captive to the main part. It can then also be provided that the articulated connection between the actuatable handle portion and the movable part can be released and a further connection is provided for securing the movable part.

According to a further advantageous development of the invention, it is provided that the movable part is displaceable in the main part by means of a guide from an initial position into a working position, and that the movable part, when changed over into a cleaning position, comes free from the guide and is at least partially pivotable about a pivot axis of the articulated connection. This constructional design can give simple handling, which makes possible a quick and simple arrangement of the movable part with respect to the main part for cleaning and disinfection and also a subsequent fitting together for surgical use. The pivotable arrangement of the movable part has the further advantage that the articulated connection between the actuatable handle portion and the movable part is likewise easily accessible for cleaning.

According to a further advantageous configuration of the invention, it is provided that on changeover of the moved part from a cleaning position into a working position, the guide section of the movable part engages in a seating of the main part, and the guides automatically engage together on pressing the actuatable handle portion. A more secure and positive construction can thereby be attained in which pressing of the actuatable handle portion takes place to an extent that the locking device can be changed over automatically or manually into the locking position, so that following this the working stroke is released for the movable part.

According to a further advantageous configuration of the invention, it is provided that the guide in the main part has a first section which runs obliquely and which moves the movable part toward the main part and changes it over into a working position. An easy bringing together and complete juxtaposition of the guide surfaces between the main part and the movable part can thereby be attained.

According to a further advantageous development of the invention, it is provided that the locking device has a latch, which is provided on the handle. A simple one-hand operation for the unlocking of the locking device can thereby be provided. The latch can be provided both on the stationary handle portion and also on the actuatable handle portion. This arrangement can be freely selected in dependence on the embodiment.

According to a further advantageous development of the invention, it is provided that a pivotable latch is provided in the stationary handle portion and engages the actuatable handle portion near a hinge pin. A compact construction can thereby be attained, being advantageously referred to the prior art geometry and size of the surgical instruments.

According to a further advantageous development of the invention, it is provided that the pivotable latch has a stop determining its locking position. The working stroke of the movable part can thereby be limited, the stroke limitation of the movable part by the latch then mostly determining the initial position of the movable part for a working stroke.

According to a further advantageous development of the invention, it is provided that the latch is pivotable into an unlocking position and releases a further pivoting region of the actuatable handle portion, which is preferably limited by a stop provided on the main part. The movable part can thereby be moved relative to the main part such that the mutually engaging guide sections can be separated from each other, in order to pivot the movable part around the articulated connection and to at least partially lift it from the main part. The size of the pivoting region can advantageously be determined in dependence on the length of the mutually engaging guides, so that even a very short pivoting region would be sufficient to separate from each other the interengaging guides between the main part and the movable part.

According to a further advantageous development of the invention, it is provided that the latch engages on a section between a pivot axis of the actuatable handle and the articulated connection. A compact construction can thereby be provided, and the latch can be integrated nearly completely into the stationary handle. Furthermore, this locking device is not troublesome for the other manipulations.

According to a further advantageous development of the invention, it is provided that the latch has a locking section which engages at a complementarily constructed pivot section of the actuatable handle. A defined arrangement of the pivot section on the locking section can thereby be given. It can advantageously be thereby attained that, by the formation of a kind of undercut or of an abutment surface and an adjoining detent cam, on returning the actuatable handle portion to its initial position after each working stroke, the latch is pressed into a locking position. Should the latch have been released even only slightly from its locking position, it is automatically brought back again into this after each working stroke. A secure manipulation can thereby be ensured. The arrangement of the latch on the stationary handle has the further advantage that a transition region which nearly completely shuts off the locking mechanism is provided between the stationary handle and the main part, so that this locking device can at the same time be protected against mechanical damage from the exterior.

Further advantageous configurations and developments of the invention are described in detail in the further claims.

Advantageous embodiments are described in more detail with reference to the accompanying drawings.

BRIEF DESCRIPTION OF THE DRAWINGS

FIG. 5 shows a schematic side view of an embodiment according to the invention with an alternative locking device, FIG. 6 shows a schematic side view of an embodiment according to the invention with a further alternative locking device.

DETAILED DESCRIPTION OF THE INVENTION

A first embodiment of a surgical instrument 11 according to the invention is shown in FIGS. 1–4. This surgical instrument 11 for example concerns a so-called punch, which is used in surgical operations for the removal of tissue, bones, or the like. The invention is not limited to these punches, but can be carried over to all surgical instruments which have the same problems regarding cleaning and sterilization and also the allocation of components.

Figure 1:
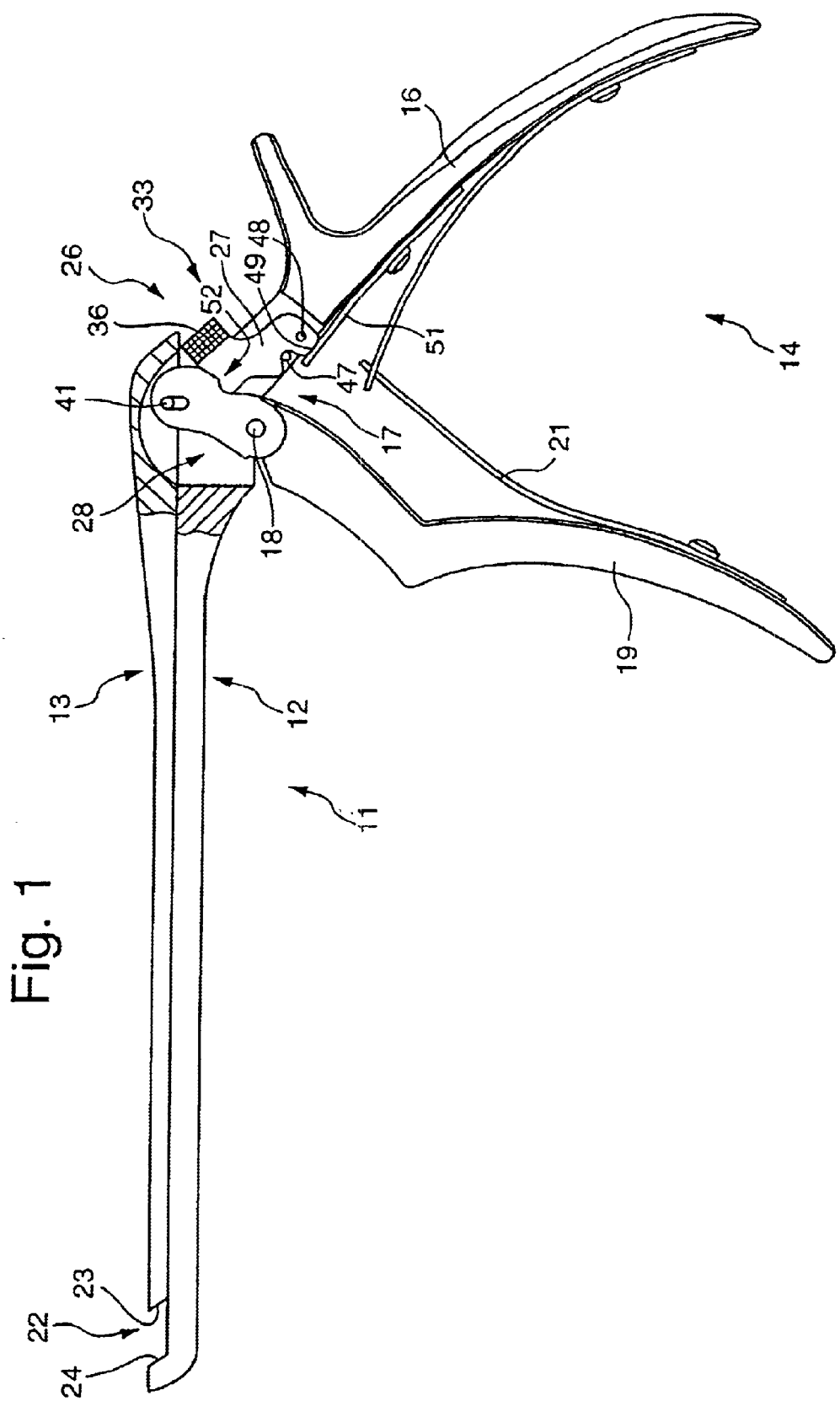
FIG. 1 shows a schematic side view of an embodiment according to the invention in an initial position.

The surgical instrument according to FIG. 1 has a main part 12 which receives a movable part 13 which is displaceable relative to the main part 12.

A handle 14 is arranged on the main part 12. The main part 12 merges into a stationary handle portion 16 of the handle 14 and has a hinge pin 18, around which an actuatable handle portion 19 is arranged to be pivotable, in the transition region 17 from the main part to the stationary handle portion 16. The actuatable handle portion 19 and stationary handle portion 16 are arranged in an initial position 22 by means of a spring 21. The cutting elements 23, 24 are spaced apart in this initial position 22, this spacing being determined by the maximum path of a working stroke. This initial position 22 is furthermore determined by a locking device 26. A latch 27 of the locking device 26 limits the pivoting movement, effected by the spring element 21, of the actuatable handle portion 19 around the hinge pin 18. A shorter lever section 28 then abuts on the latch 27.

On actuation of the handle portion 19, this is pivoted around the hinge pin 18, the movable part 13 being moved to the left in the drawing, in order to move the cutting element 23 toward the cutting element 24.

Figure 2:
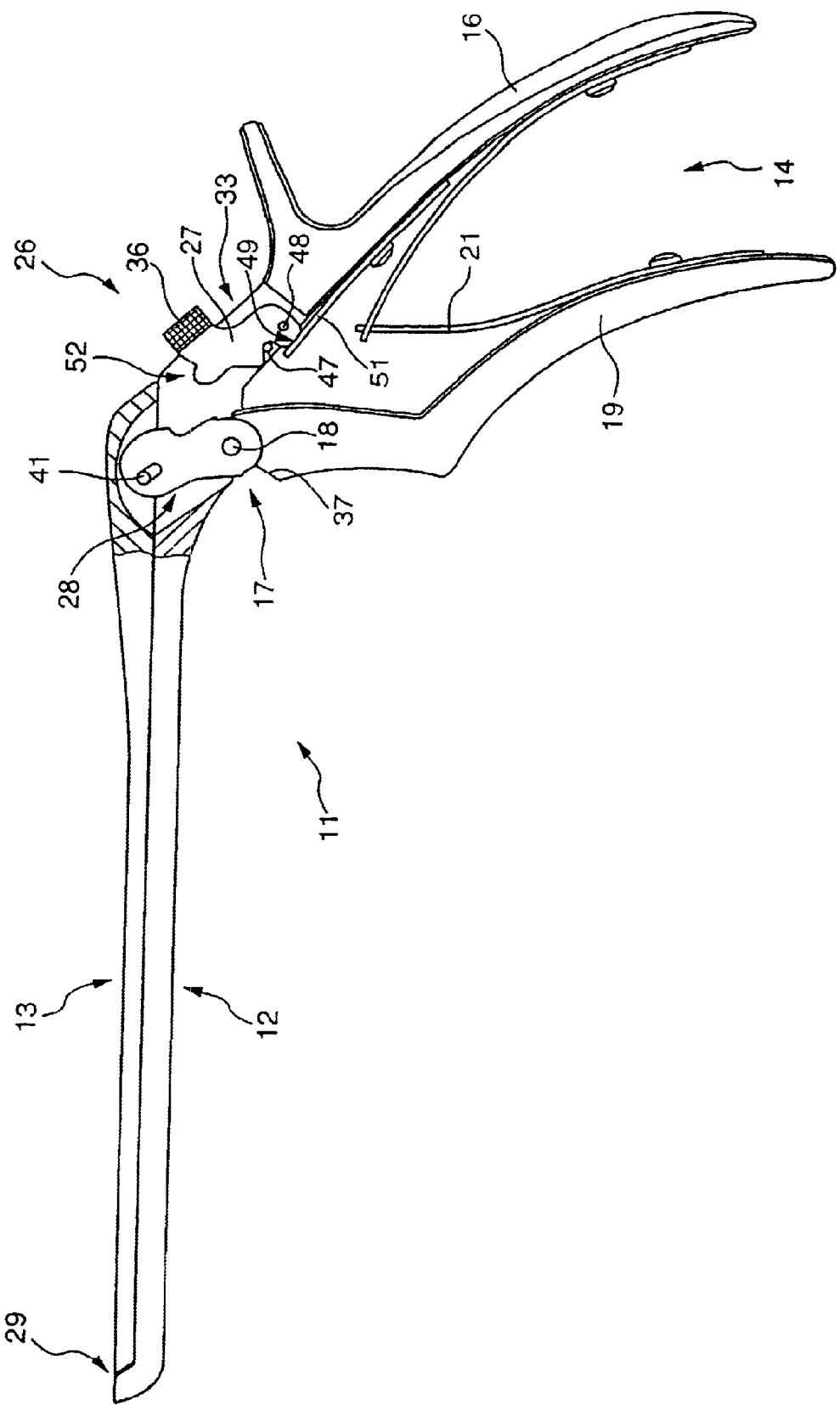
FIG. 2 shows a schematic side view of the embodiment according to FIG. 1 in a working position.

In FIG. 2, the working stroke has ended and the surgical instrument 11 is shown in a working position 29. The tissue or bone or the like to be removed is enclosed within a cavity provided within the cutting elements 23, 24, and thus can be removed. After the surgical instrument 11 has been removed from the region of the surgical operation, the handle 14 can be released, whereupon the surgical instrument 11 is automatically positioned in an initial position 22 by means of the spring element 21. The material to be removed can then be automatically released from the cutter 23, since the guide elements 31, 32 advantageously serve as an ejector.

The guide element 31 on the moving part 13 is shown as an example in FIG. 4. This spring, preferably T-shaped, engages in a corresponding groove, which forms the guide element 32, in the main part 12. The guide elements 31, 32 can also be adapted and constituted in dependence on the constitution of the surgical instrument 11.

For cleaning and disinfecting the surgical instrument 11, it is required that the movable part 13 is at least partially lifted from the main part 12, in order to also clean and disinfect the interspaces. The locking device 26 is shown changed over from its locking position 33, as shown in FIGS. 1 and 2, into its unlocking position 34 according to FIGS. 3 and 4. According to the embodiment in FIGS. 1–4, this takes place by pivoting of the latch 27; advantageously, the actuatable handle 19 is moved at least partially toward the stationary handle 16, so that the latch 7 can be pivoted into the unlocking position by means of the handle portion surface 36. A further extent of path is thereby freed for the movable part 13, so that the latter is displaceable with respect to the main part 12 such that the guide elements 31, 32 are mutually released. This displacement path is limited by a stop 37 provided on the actuatable handle 19 and cooperating with a corresponding surface in the transition region 17.

The movable part 13 and the actuatable handle portion 19 are advantageously actively connected by means of an articulation 41. This articulation 41 is constituted as a pivotable articulation which at the same time makes possible a longitudinal movement of the hinge pin, in order to make possible an arcuate movement of the lever section 28 around the hinge pin 18 in a longitudinal movement of the movable part 13 along the main part 12.

Figure 3:
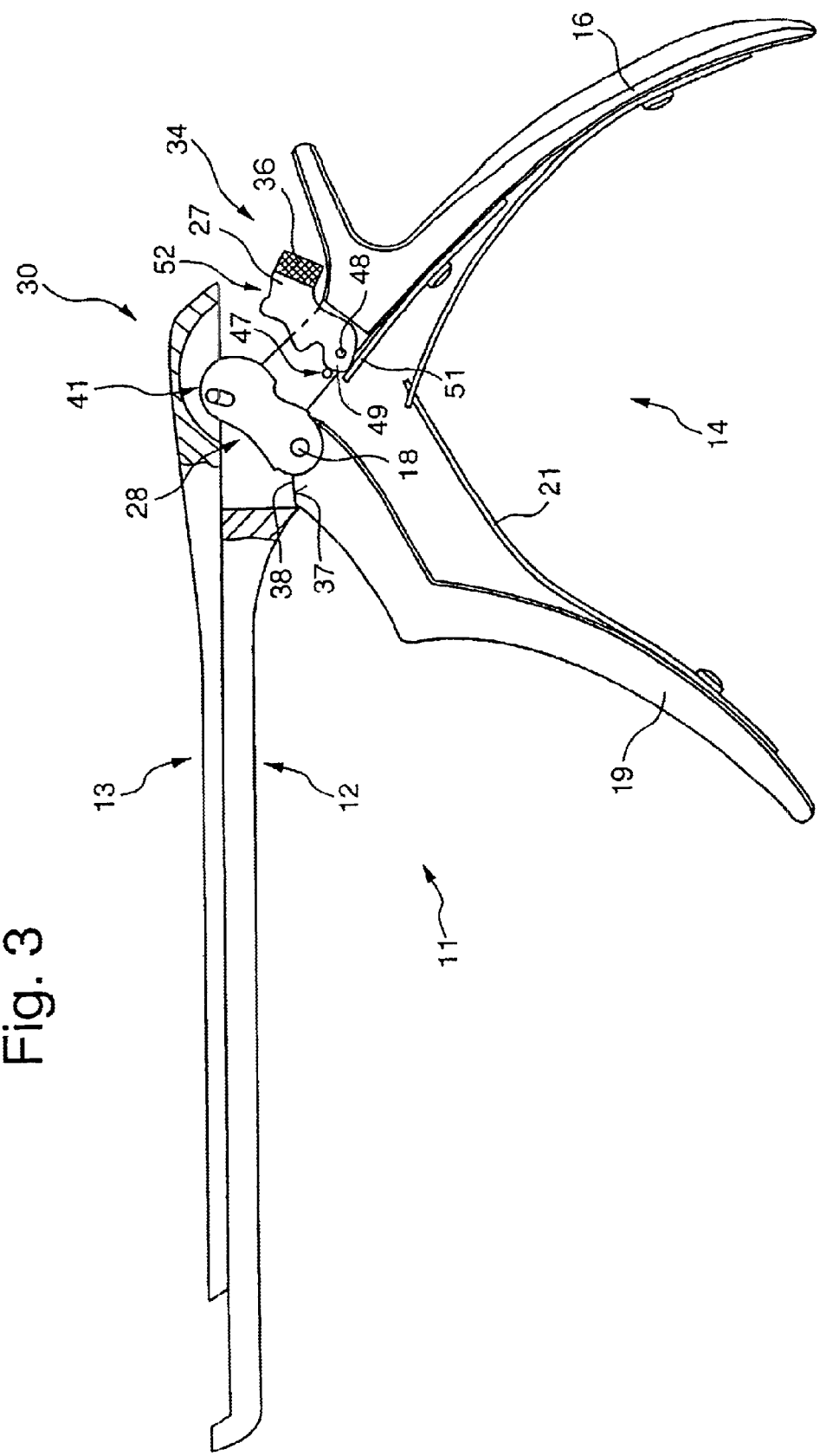
FIG. 3 shows a schematic side view of the embodiment according to FIG. 1 in an intermediate position, with unlocked locking device.
Figure 4A:
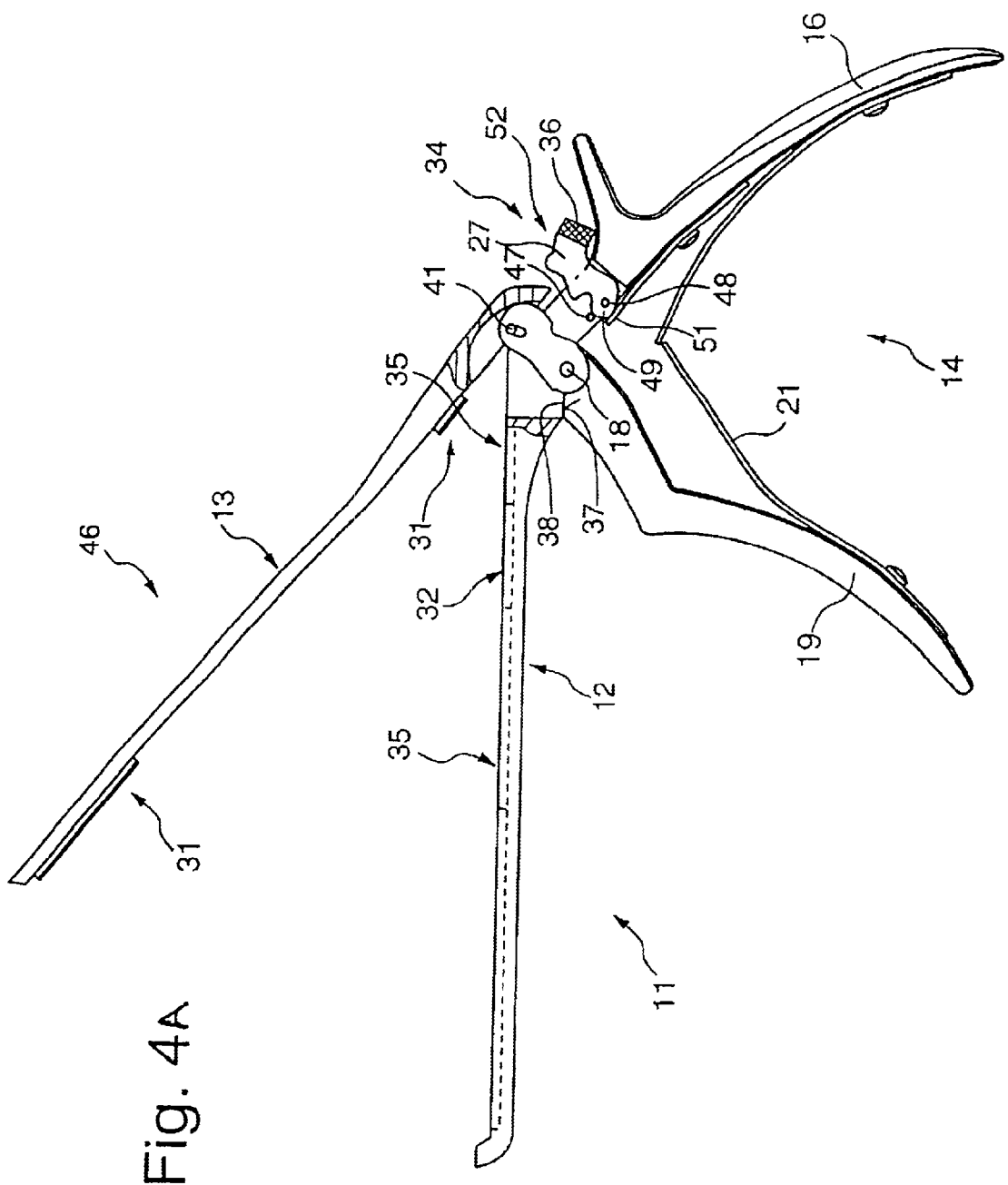
FIG. 4a shows a schematic side view of the embodiment according to FIG. 1 in a cleaning position.

An intermediate position is shown in FIG. 3, and is passed through during the changing over of the surgical instrument from an initial position 22 according to FIG. 1 into a cleaning position according to FIG. 4a. After the unlocking of the latch 27, the movable part 13 is transferred into the intermediate position 30 according to FIG. 3, in order to then change over into the cleaning position according to FIG. 4 by pivoting of the movable part 13 around the articulation 41. This can take place by simple actuation or pressing of the end section toward the connection 41, in order to lift up the movable part 13 from the main part 12. This arrangement has the advantage that the interspaces between the movable part 13 and the main part 12 are easily accessible and furthermore the components of the surgical element are coupled together.

Figure 4B:
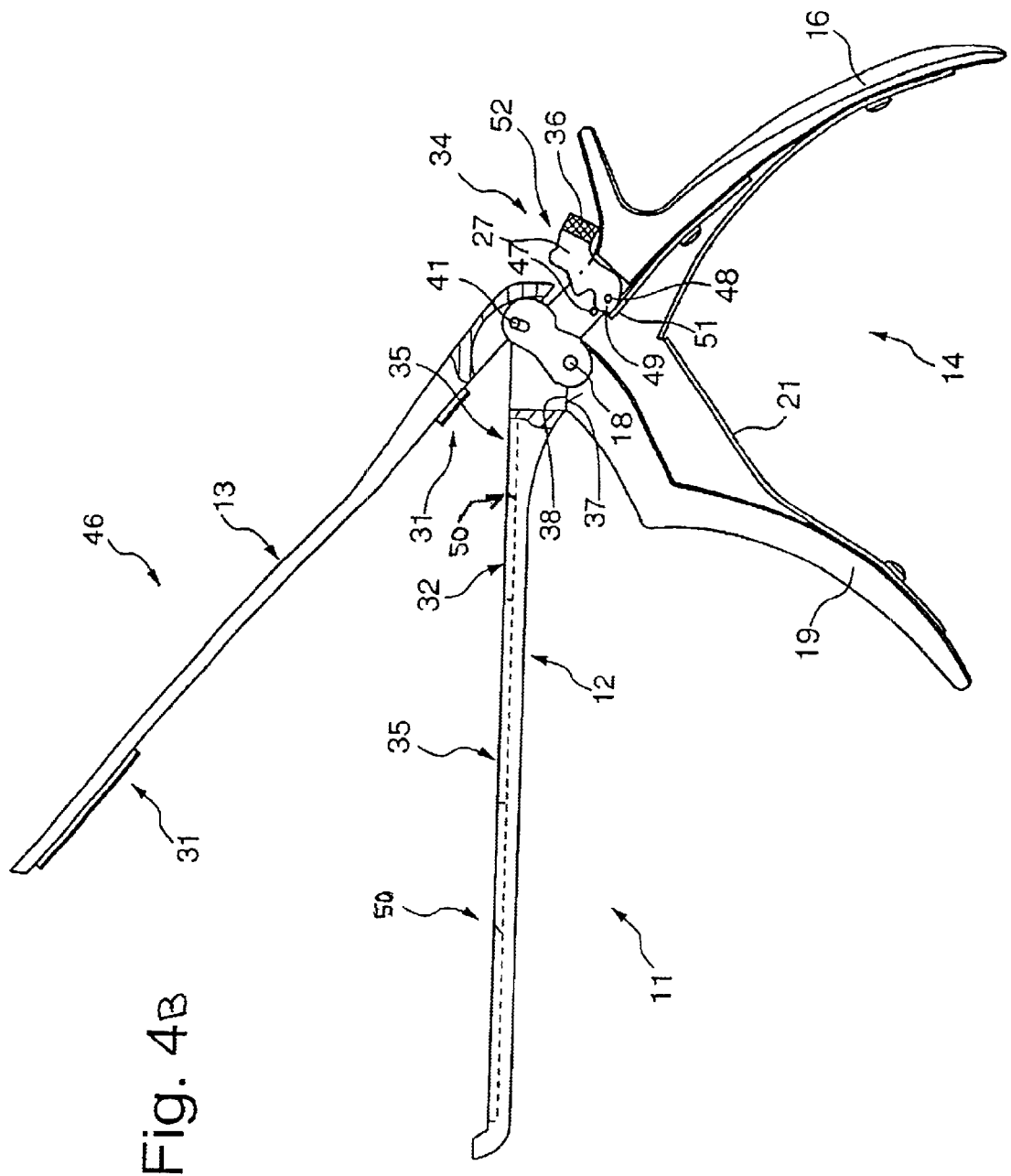
FIG. 4b shows a schematic side view of the embodiment according to FIG. 1 with an alternative guide.

The operation of bringing the surgical instrument 11 into readiness for use takes place in the reverse sequence. The movable part 13 is first moved toward the main part 12, with the guide element 31 engaging in a seating 35 of the main part 12, which then merges into the guide element 32. The actuatable handle portion 19 is then moved toward the stationary handle portion 16, due to which the guide element 31 engages in the guide element 32. A first section of the guide element 32 is advantageously arranged obliquely as shown in FIG. 4b by reference number 50, so that the movable part, during the axial movement in the direction of the cutter 24, is simultaneously moved downward toward the main part 12, so that a nearly seamless transition between the movable part 13 and the main part 12 is provided in the initial position. The latch 27 is transferred into its locking position 33, thus abutting on a bounding element 47. The latch 27 can thereby be transferred into a defined position which at the same time determines the initial position 22, since the spring element 21 moves the actuatable handle around the hinge pin 18, due to which the lever section 28 abuts on the latch 27.

The latch 27 is arranged to be pivotable around a shaft 48. A lug 49 is provided near the shaft 48 and cooperates with a spring 51. This spring 51 on the one hand has the effect that during the actuation of the surgical instrument 11, the latch 27 is kept in its locking position 33, and also that it is held in an unlocking position 34 during cleaning. The lug 49 is accordingly constituted so that both end positions can be fixed.

The latch 27 furthermore has an abutment section 52 which is composed of a rectilinear section and a semicircular section. This configuration can be variably constituted, for example as an undercut, the function having to be fulfilled according to which, during the movement of the actuatable handle portion 19 out of the working position 29 into an initial position 22, the lever section 28 acts on the latch 27 such that the latter is moved toward the bounding element 47. It can thereby be ensured that after each working stroke the latching element, possibly being partially loosened, is guided back again into the locking position 33.

Alternatively to the embodiment according to FIGS. 1 and 4, it can be provided that the stationary handle portion 16 and the actuatable handle portion 19 are interchanged. The locking mechanism can also be arranged analogously to this. It is likewise conceivable that, instead of the latch 27 which holds the initial position 22 due to a pressure loading, this also holds due to a tensile loading, for example, when the locking element is arranged mirror-imagewise to a line which, for example, would be formed between the hinge pin 18 and the articulation 41.

It can alternatively be provided that instead of an articulated connection such as is shown in FIGS. 1–4, a U-shaped opening or the like is provided, by means of which a bolt or a pin which is arranged on the movable part 13 runs in the guide in the lever section 28 of the actuatable handle portion 19. In addition, in order to associate the movable part 13 in a captive manner with the main part 12 or with the handle 14, a further securing element, such as for example a cord, a chain, or a further bar-shaped articulated connection can be provided, in order on the one hand to be capable of being dismantled for cleaning and disinfection, and on the other hand for the movable part 13 to be associated in a captive manner with the further components of the surgical instrument.

An alternative embodiment of a locking device is shown in FIG. 5. A latch 57 is arranged pivotably on the stationary handle 16 and crosses the actuatable handle portion 19. It is thereby advantageously provided that a recess 58, in which the latch 57 is guided, is provided in the handle portion 19: This latch 57 has a seating 59 by means of which the movable part 13 can be associated with the main part 12 in an initial position. This locking can be released by pressing the latch 57, so that a further pivoting region is freed for the handle portion 19 in order to change the movable part 13 over into an intermediate position 30 according to FIG. 3, to then be able to be pivoted into a position 46 according to FIG. 4. The widened pivoting region of the handle portion 19 can on the one hand be limited by a stop 37 on a surface 38 of the main part, or by a further detent lug which is provided on the latch 57. The latch 57 is pushed or pulled by a spring, not further described, toward the hinge pin 18, and is yieldable during the actuation of the surgical instrument 11, so that the handle portion is provided pivotably toward the stationary handle portion 16.

It can alternatively be provided that the detent lug also engages on a lower section of the recess 56. In order to transfer the surgical instrument 11 from an initial position 22 into a cleaning position 46, it is required in this case that the latch 57 be moved upward.

It will be understood that this arrangement can also be provided in a mirror image fashion, both as regards the arrangement of the latch and as regards the handle portions 16, 19. This is also true for the further embodiments.

A further alternative locking device 66 is shown in FIG. 6. This locking device 66 has a latch 67 which engages on a rear end of the movable part 13 and limits the movement along the main part 12. The latch 67 can be transferred from a locking position 33 as shown in FIG. 6 into an unlocking position, not further shown, by means of a sliding movement toward the free end of the handle portion 16, or by a pivoting movement, which is conceivable in each direction, around a rotation axis. The movable part 13 can thereby be changed over from the working position 22 shown in FIG. 6 into the intermediate position 30 shown in FIG. 3. It can likewise be provided that the latch 67 engages, instead of a stop shown according to the drawing, even directly on the lever section 28, for example, near the articulation 41. The latch 67 can likewise be provided on the moved part 13 and can cooperate with the handle 14 or the main part 12.

Figure 7:
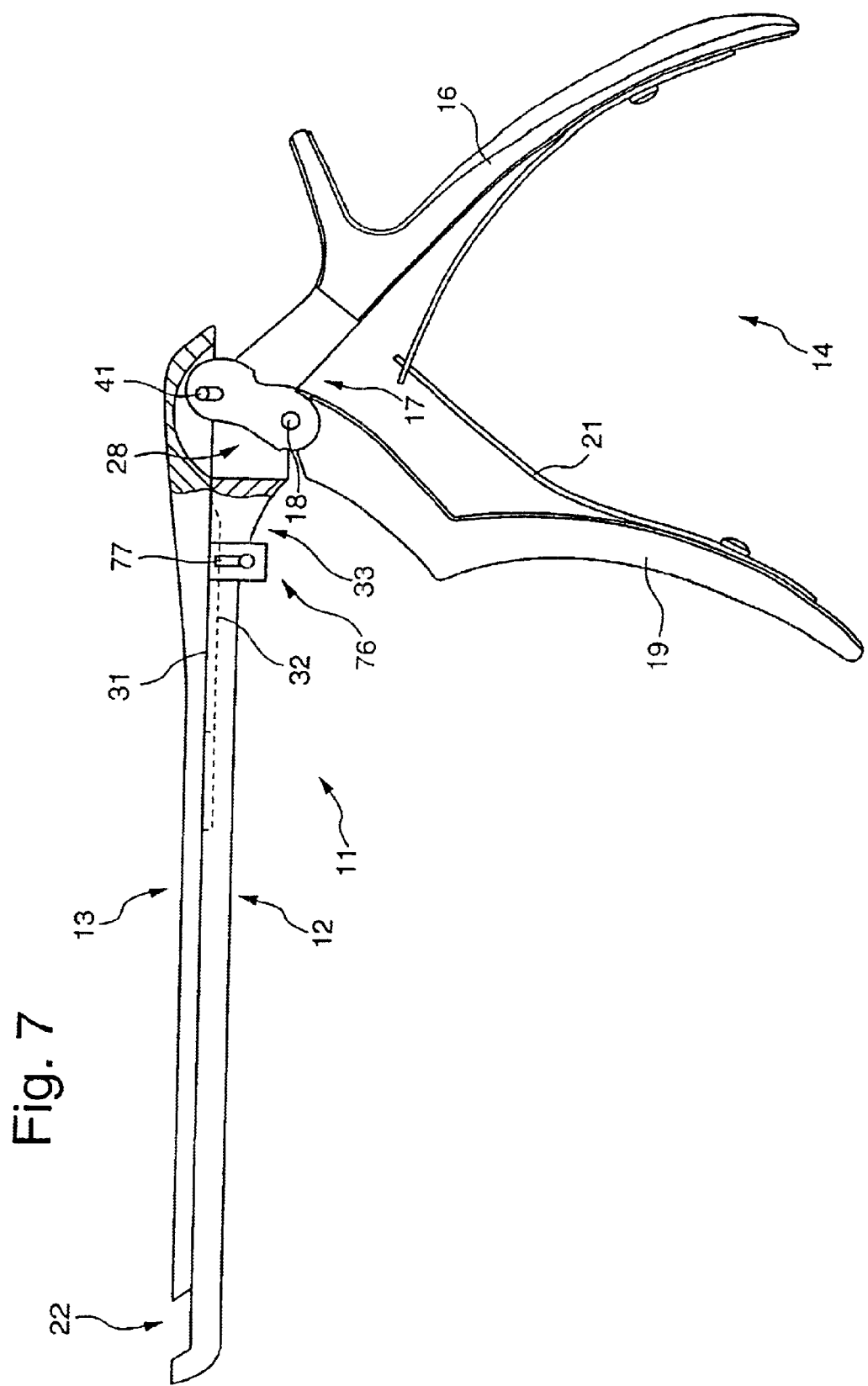
FIG. 7 shows a schematic side view of an embodiment according to the invention with a further alternative locking device.

A further alternative embodiment of a locking device 76 is shown in FIG. 7. This locking device 76 is provided on the main part 12 and engages in the guide element 32 or a seating 35. In a locking position 33 this locking device 76 blocks, by means of a latch 77, the movement of the movable part 13 toward the right in the illustration, or into an initial position 22. The latch 77 can be actuated by pushing, pulling, sliding or folding around a rotation axis and can release the guide element 32, so that the guide element 31 can be guided out of the guide element 32.

All the embodiments have in common that the movable part 13 can be associated movably and removably with respect to the main part 12, the movable part being provided in a captive manner with respect to the main part, by means of a connection. The locking device can be provided, in dependence on the embodiment, on the stationary handle portion 16, the actuatable handle portion 19, the main part 12, or the movable part 13, and can engage in a locking position on respectively at least one adjacent part or handle portion. The locking device can be locked and unlocked by means of pulling, sliding, pressing, folding, pivoting, or the like, of a latch. It will be understood that the corresponding materials suitable for surgical instruments are used.

Alternatively to the surgical elements shown in FIGS. 1–7, which are constituted as so-called upper-cutting punches, under-cutting punches can also be provided. The cutters 23, 24 are provided on the main part 12 in a fashion mirror-image to the guide plane of the movable part 13. These embodiments can likewise be constituted according to the invention. The movable part 13 is then constituted in a stepped form, a first section in the region of the articulation 41 being retained and a section leading to the cutter 23 running on the underside of the main part 12. So that the same configuration according to the invention can be made possible and the advantages resulting therefrom can be attained, it is provided that an articulation is provided in the step-shaped transition region from the upper side to the lower side, whereby the forward step-shaped offset section can be pivoted away with respect to the main part 12 into an intermediate position according to FIG. 3, in order to be subsequently pivotable according to FIG. 4. Such modifications or supplementary measures in order to make use of the advantages according to the invention are likewise included according to the invention.

What is claimed is:

1. Surgical instrument comprising a main part (12), at least one part (13) movable relative thereto, a handle (14) arranged on the main part (12) and having a stationary handle portion (16), an actuatable handle portion (19) which actuates the movable part (13), and a locking device (25, 56, 66, 76) in which in a first position the movable part (13) is arranged in an initial position (22) and in a second position (34) the movable part (13) is changed over into a cleaning position (46); wherein the movable part (13) is arranged captive to the main part in the cleaning position (46); and the moveable part (13) and the actuatable handle portion (19) are arranged pivotably to each other by means of a jointed, slide, or hinge type articulated connection (41).

2. Surgical instrument according to claim 1, wherein the movable part (13), on changing over from the initial position (22) into the cleaning position (46), gets free from a guide (32) of the main part (12) and is at least partially pivotable around a pivot axis of the connection (41) between the actuatable handle portion (16) and the main part (12).

3. Surgical instrument according to claim 1, wherein, upon changing over the moveable part (13) from the cleaning position (46) to the initial position (22), guides (31) of the movable part (13) engage in a guides (32) of the main part (12), and by pressing the actuatable handle portion (19), the guides (31) of the moveable part (13) and the guide (32) of the main part (12) automatically engage in each other.

4. Surgical instrument according to claim 3 wherein the guide of the main part (32) has a first section which runs obliquely in the main part (12) to introduce the guides (31) of the movable part (13) toward the main part (12) by changing from the cleaning position (46) into the initial position (22).

5. Surgical instrument according to claim 1, wherein the locking device (25, 56, 66, 76) has a latch (27, 57, 67, 77) which is at least one of frictionally and positively disposed at least in a locking position (33).

6. Surgical instrument according to claim 5, wherein an additional rotating movement of the actuatable handle portion (19) is enabled by positioning the latch 27 in an unlocking position (34) and the additional rotating movement is limited by a stop (37) provided on the main part (12).

7. Surgical instrument according to claim 5, wherein the latch (27) engages on a lever section (28) between a hinge pin (18) and the articulated connection (41).

8. Surgical instrument according to claim 5, wherein the latch (27) has a locking section which engages on a lever section (28) of the actuatable handle portion (19), which has a complementarily constituted section to the locking section.

9. Surgical instrument according to claim 8, wherein the locking section has an abutment section (52), which abuts an adjoining section on the actuatable handle portion (19).

10. Surgical instrument according to claim 1, wherein the locking device (26, 56, 66) has a latch (27, 57, 67) which is provided on the handle (14).

11. Surgical instrument according to claim 10, wherein the latch (27, 57, 67) is provided on the stationary or actuatable handle portion (16, 19).

12. Surgical instrument according to claim 1, wherein the locking device has a pivotable latch (27) provided on the stationary handle portion (19) and engages the actuatable handle portion (19) near a hinge pin (18).

13. Surgical instrument according to claim 1, wherein the locking device has a pivotable latch (27) having a bounding element (47) determining its locking position (33).

14. Surgical instrument according to claim 1, the locking device is a latch the latch (57) engages a section of the actuatable handle portion (19) opposite the lever section (28).

15. Surgical instrument according to claim 14, wherein the latch (57) is guided in a recess (58) of the actuatable handle portion (19).

16. Surgical instrument according to claim 15, wherein a shoulder (59) is provided on the latch (57) and positions the actuatable handle portion (19) in an initial position (22).

17. Surgical instrument according to claim 14, wherein by releasing locking device at the shoulder (59), the latch (57), and an edge region of the recess (58), a further pivoting region of the actuatable handle portion (19) is released and the actuatable handle portion (19) is pivotable as far as a step (37) on the main part (12) or a further stop of the latch (57).

18. Surgical instrument according to claim 14, wherein on changing over the actuatable handle portion (19) from a cleaning position (46) into a working position (22) an automatic locking of the latch (57) is provided and the actuatable handle portion (19) is arranged in an initial position.

19. Surgical instrument according to claim 1, wherein the locking device is a latch (67) is provided on the stationary handle portion (16) and engages on the movable part (13) at an end section of the movable part (13).

20. Surgical instrument according to claim 19, wherein the latch (67) is constituted pivotably or displaceably.

21. Surgical instrument according to claim 19, wherein the latch (67) is secured in a locking position (33) by means of a releasable detent connection.

22. Surgical instrument according to claim 1, wherein the locking device (67) has a latch (77) which is provided on the main part (12) or on the movable part (13).

23. Surgical instrument according to claim 22, wherein the locking device (76) provided on the main part (12) has a latch (77) which engages in a guide (32) in the main part (12), in which the guide is guided at least section-wise.

24. Surgical instrument according to claim 22, wherein the latch (77) is provided on a region limiting a working stroke of the movable part (13).

25. Surgical instrument according to claim 22, wherein the latch (77) is releasable by means of a pressing, pulling, or sliding mechanism.

* * * * *